United States Patent
Wardlaw et al.

(12) 
(10) Patent No.: US 6,518,038 B1
(45) Date of Patent: *Feb. 11, 2003

(54) DETECTION AND QUANTIFICATION OF ONE OR MORE TARGET ANALYTES IN A SAMPLE USING SPATIALLY LOCALIZED ANALYTE REPRODUCTION

(75) Inventors: Stephen C. Wardlaw, Lyme, CT (US); Stephen C. Edberg, Orange, CT (US)

(73) Assignees: Robert A. Levine, Guilford, CT (US); Ward Law Partners LP., Lyme, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/728,826

(22) Filed: Nov. 28, 2000

(51) Int. Cl.$^7$ ................................................. C12Q 1/04
(52) U.S. Cl. ......................... 435/34; 435/30; 435/287.2
(58) Field of Search ............................... 435/4, 29, 34, 435/287.1, 287.2, 30

(56) References Cited

U.S. PATENT DOCUMENTS 5,168,063 A * 12/1992 Doyle et al.
5,294,537 A * 3/1994 Batt
6,007,990 A * 12/1999 Levine et al.

OTHER PUBLICATIONS

WO 86/01805. Wright et al. (1986). Monoclonal antibodies and their use.*

JP 03133394A. Aoyama et al. (1991). Monoclonal antibody for diagnosing Candida albicans in cell, etc.*

* cited by examiner

Primary Examiner—Ralph Gitomer
(74) Attorney, Agent, or Firm—William W. Jones

(57) ABSTRACT

The presence or absence of one or more target microbial analytes in a substance, such as a biological or environmental substance, is assayed by inoculating a growth medium with a sample of the substance. The medium may be combined with a labeled analyte-specific material (LASM) which can migrate through the substrate and which is homogeneously distributed throughout the medium. The LASM may be premixed with the medium, or may be added to the medium after inoculation with the substance. The nature of the medium is such that it will support target analyte reproduction so as to form target analyte colonies in or on the medium, and it will not allow the target analyte colonies to migrate on or within the medium. After the sample to be assayed is added to the medium, growth of the target analyte colonies in the sample will bind increasing quantities of the LASM, thereby creating localized intensely labeled areas in the medium which can be visually or photometrically detected. As the target analyte colonies grow on or in the medium they attract increasing quantities of the LASM which diffuses to the colonies through the medium causing the local target analyte colonies to become intensely labeled, which renders the colonies readily detectable. Each of the intensely labeled target analyte colonies in the medium may also be surrounded by areas of lower intensity due to local depletion of the LASM in the regions of colony growth. The number of intensely labeled target analyte colonies in the medium will be proportional to the concentration of the target analyte present in the sample. In the event that the target analyte is absent from the sample, then there will be no localized labeled microbe colonies in the medium.

26 Claims, 4 Drawing Sheets

DETECTION AND QUANTIFICATION OF ONE OR MORE TARGET ANALYTES IN A SAMPLE USING SPATIALLY LOCALIZED ANALYTE REPRODUCTION

TECHNICAL FIELD

This invention relates to a method and paraphernalia for visually or photometrically detecting the presence or the absence of one or more microbial target analytes in a material sample; and enumerating the analyte(s) when found to be present in the sample. The material being analyzed can be a biological material; an environmental material; a food stuff material; or some other material which can harbor the target analyte(s). The target analyte(s) is (are) one or more specific living organisms such as microbes, bacteria, fungi, mycoplasma or protozoa which may be found in the material being tested; and the presence or absence of the target analyte or analytes is determined by causing metabolic reproduction of the target analyte or analytes in a suitable growth medium. The analysis can be performed in a gel or a semi-solid growth material which supports selective growth of the target analyte(s), but restricts growth of other viable organisms which may be in the sample. In this manner, detectable target analyte colonies are formed in the medium. The colonies may be detected and counted by various techniques, including the use of visually or photometrically detectable materials which will selectively bind to some portion of the target analyte(s).

BACKGROUND ART

The analysis of specimens for the presence or absence of target bacteria and other viable organisms such as fungi and protozoa, wherein the specimen is placed on a sterile growth medium, is well known. Various bacteria are usually differentiated by their appearance, their chemical reaction with growth or other medium, or by applying an enzymatic or immunological reactant. Since bacterial colonies of different species appear similar, it is usually necessary to perform a number of tests on a number of colonies before one can be establish a correct identification. This is especially a problem if it is necessary to distinguish bacterial subspecies, for example, finding the location of a colony of *E. coli* serotype 0157:H7 within a mix of other, apparently identical *E. coli* colonies. There are growth medium with specialized characteristics which help in the rapid visual location of such organisms, but the more closely related the target organism is to the background, the more difficult it is to distinguish them on chemical tests alone. It would be highly desirable if such colonies could be rapidly and specifically located, particularly if no additional operations were required by the technician.

DISCLOSURE OF THE INVENTION

This invention relates to a method and paraphernalia for detecting the presence or absence of one or more target microbial analytes in a sample. Detection of the target analyte is accomplished by growing the target analyte in a nutrient medium so as to form colonies of the target analyte in the medium, and then detecting and counting any resultant target analyte colonies which may form in the medium.

The analysis is performed in a medium which may also contain, or is combined with, one or more labeled analyte-specific materials (LASMs). The LASMs are homogeneously distributed throughout the medium The LASMs include a binding element, which may be a protein, lectin or a nucleotide sequence that is specific to a binding site in or on the target analyte. The label may be a dye or a fluorophore, including a colloid or particle, which is attached to the binding element. The LASMs in the medium can diffuse and migrate through the medium to the target analyte colonies, and will bind to the individual organisms in the colonies thereby differentially highlighting the colonies relative to the remainder of the medium. The LASMs may either bind directly to the surface of the organism, or to a product of the organism, such as its capsular material or an internal molecular structure, so long as the LASM, being so bound, does not appreciably migrate away from the site. Because the binding of the LASMs locally depletes the LASM concentration in the regions of the medium occupied by the target analyte colonies, a "halo" of lower LASM concentration will form around each target analyte colony, and at the center of each halo will be a high intensity peak corresponding to the labeled colony. Any non-target organisms present in the medium will not bind the LASMs and will show this characteristic.

A sample of a material to be analyzed is inoculated into the medium or distributed on the medium. If a quantitative analysis is desired, the amount of the sample inoculum will be volumetrically measured. As the organisms reproduce, colonies will form and will remain in a fixed location in or on the medium. The LASMs within the medium are sized so as to be able to migrate in or through the medium. Therefore, the LASMs in the region of the of the target analyte colonies are free to move through the medium and bind to the target organisms in the colonies, or to their products. This will cause the target organism colonies to show a higher label signal than surrounding areas in the medium. The reason for this is that the target organism colonies become LASM-enriched, and the surrounding areas become LASM-depleted. The immediumtely surrounding areas in the medium, which abut the target organism colonies, will tend to emit a weakened label signal. The net result is the formation of "bright" spots surrounded by "dim" halos in the medium. In the event that there is no target analyte present in the sample, then the medium will retain a relatively even level of label signal emission, and will appear to be evenly "colored".

The assay can be completed within one to two hours after inoculating the medium with the sample if a sensitive opto-mechanical photometric reader is used such as the one described in co-pending application U.S. Ser. No. 09/255,673, filed Feb. 23, 1999; or within about eighteen hours if a visual inspection is used. Since one will know the volume of the sample inoculated into or spread onto the medium, one can quantify the amount of the target analyte per unit volume of the specimen sample by counting the number of highlighted colonies In the medium. This enables the use of the invention to obtain a quantitative analysis for target analyte. It is desirable that a portion of the medium which contains the LASM be protected against sample inoculation, thus allowing this portion of the medium to serve as a negative control.

Some samples, especially those from "dirty" sources, such as environmental samples, or those containing a great deal of other materials, may have a large variety of particles or other material that may have some level of non-specific signal, and where these non-specific signals may be confused with those from the target analytes. This problem can be overcome, however, by visually or photometrically taking sequential images from the same areas in the medium, which images are separated from each other by suitable periods of time. Only those colonies formed from the target organism will increase in signal intensity by virtue of their continued growth. A comparison of successive images, preferably performed by the use of digital image processing, can separate these areas of increasing intensity from the surrounding medium. This method of kinetic analysis is the preferred method in all circumstances where a suitable photometric reading device is available because this technique provides the greatest sensitivity, the best selectivity, and the fastest time to completion of the analysis.

In order to give the greatest signal/noise ratio, it is desirable that the medium be as thin as possible, i.e., about one millimeter or less, and preferably less than about 0.50 millimeter. The concentration of the label should be such that the signal from it can just be detected from a non-inoculated area of the medium. For a visual examination, a useful signal would be one that is slightly visible using the naked eye under the appropriate lighting conditions and is not so marked so as to obscure the signal from the colonies. For automated examination, the concentration should give an intensity which has an adequate signal-to-noise ratio over a "dark" background which allows its quantitation. The exact amount must be determined based upon the photometric characteristics of the instrument used. Fluorophores such as fluorescein, sulforhodamine, and Cy-3, Cy-5 and Cy-7 can be used as labels with the photometric analysis protocol. Note that two or more target organisms can be detected using this method if the labels of the LASMs for each target can be distinguished, for example, by color, and/or light wave emissions from the LASMs.

It is therefore an object of this invention to provide a method and apparatus which can be used to assay a specimen sample for the presence or absence of a target analyte.

It is another object of this invention to provide a method and apparatus of the character described wherein the sample is placed on a medium which is combined with a target analyte-specific labeled material that can migrate within the medium.

It is a further object of this invention to provide a method and apparatus of the character described wherein the target analyte is a living organism.

It is another object of this invention to provide a method and apparatus of the character described which can detect two or more target analytes on the same medium.

It is an additional object of this invention to provide a method and apparatus of the character described wherein the target analyte is detected by growing colonies of the target analyte in the medium, and thus creating increasingly localized concentrations of the analyte-specific labeled material in the colonies of the target analyte.

These and other objects and advantages of the invention will become more readily apparent from the following detailed description of the invention when taken in conjunction with the accompanying drawings, in which:

DETAILED EXAMPLE FOR CARRYING OUT THE INVENTION

Figure 1:
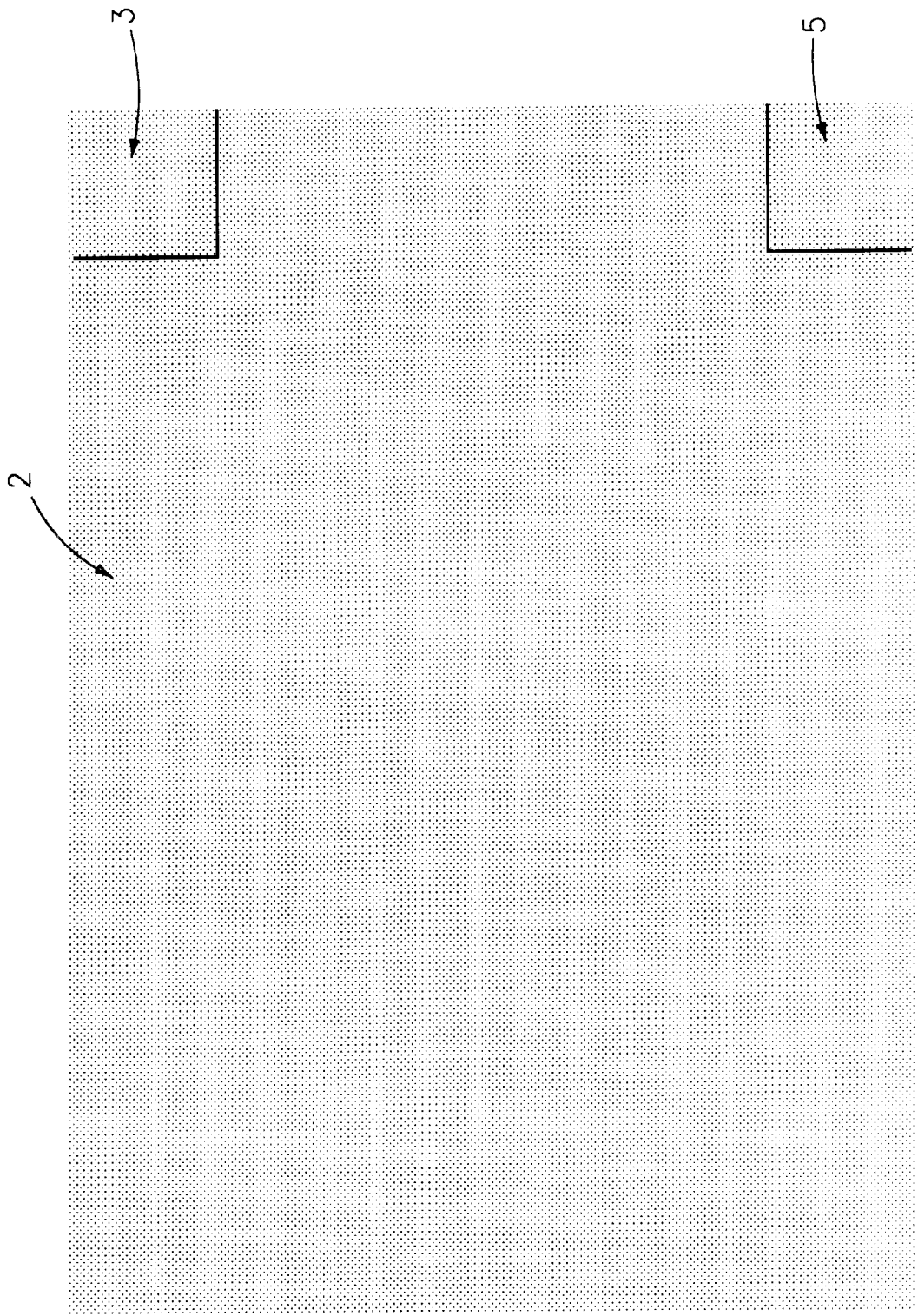
FIG. 1 is a plan view of a labeled target analyte-specific material and target analyte growth medium mixture formed in accordance with this invention.
Figure 2:
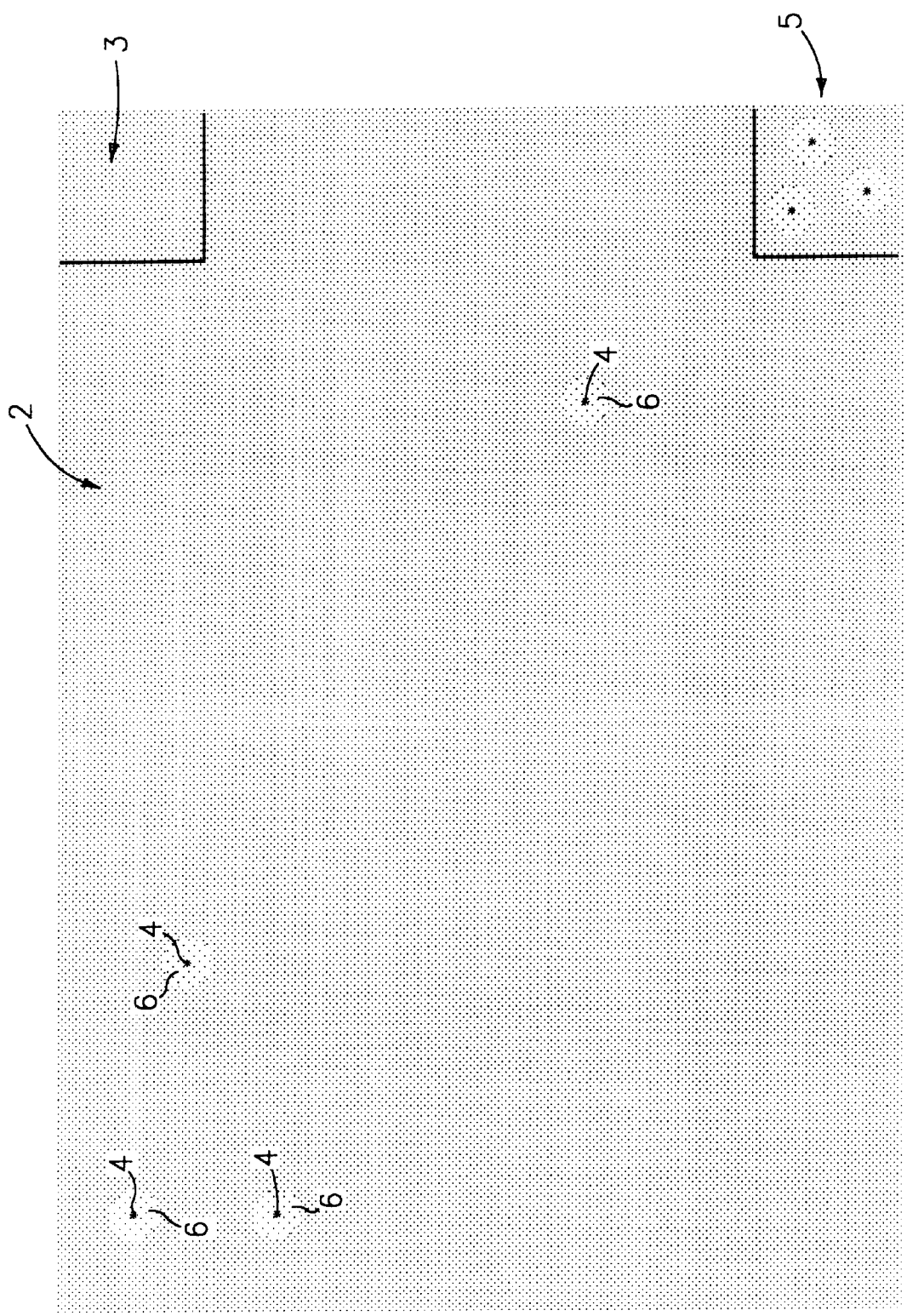
FIGS. 2 and 3 are plan views similar to FIG. 1 but showing the formation of varying degrees of localized intensely labeled areas in the mixture due to the presence of the target analyte in the sample being assayed.
Figure 3:
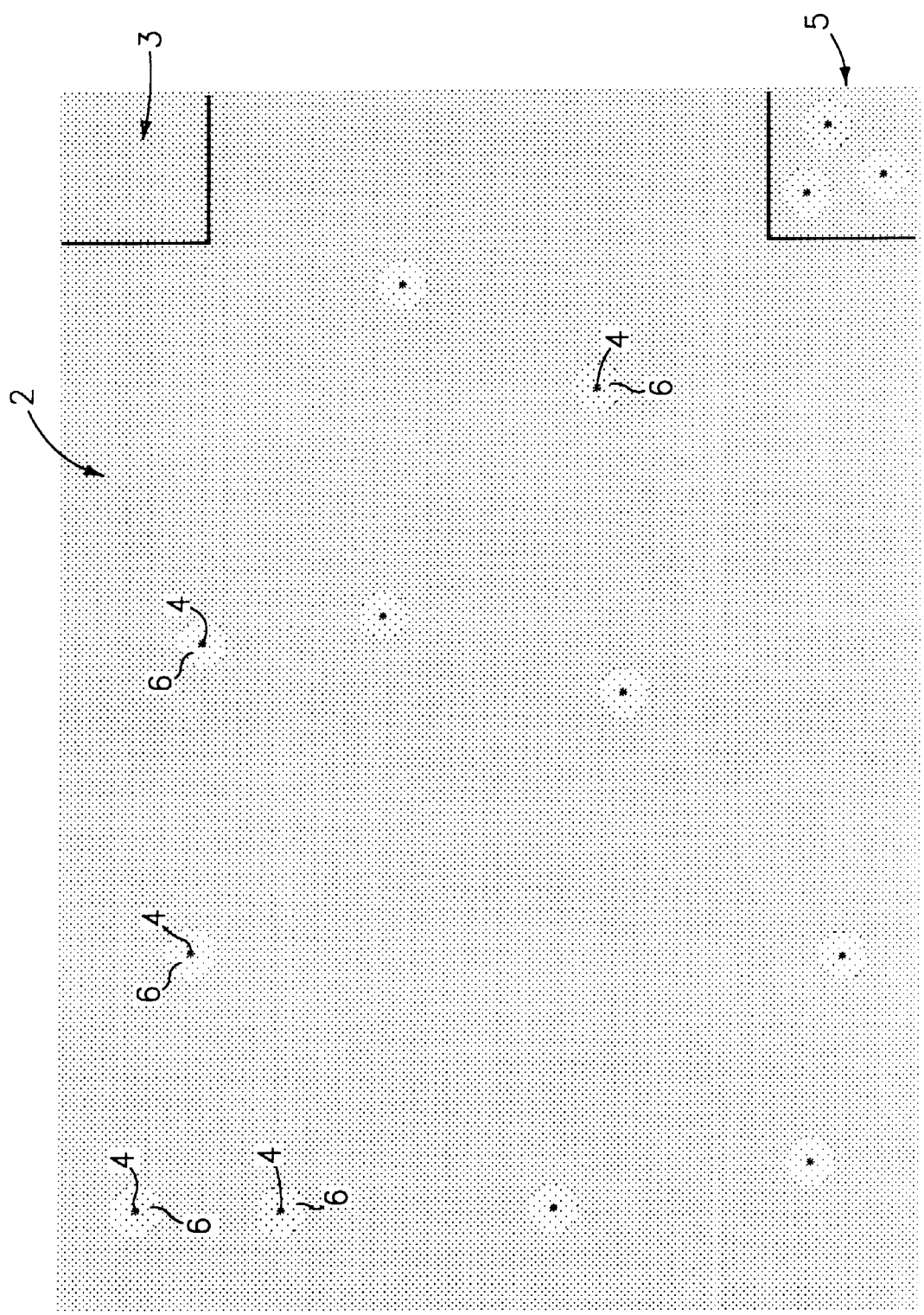
Figure 4:
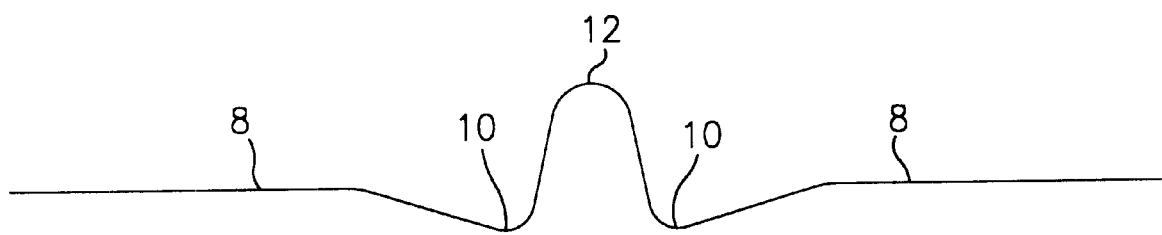
FIG. 4 is a pictograph trace of the signal intensity levels emanating from the sample as the latter is scanned by a photometric light emission signal detection instrument, or of the visually observed signal intensity levels.

Referring now to FIG. 1, there is shown a plan view of a rectangular section of a medium, denoted generally by the numeral 2, which is adapted for performing the method of this invention. The medium field as shown in FIG. 1 is evenly shaded so as to indicate an evenly distributed label signal emission which will be detected by the human eye or by a scanning instrument either before the medium has been inoculated with the sample; or after inoculation and incubation of the sample when there is no target analyte present in the sample. The area 3 in the medium 2 is an area which will not be inoculated with the sample being assayed, but which contains all of the reagents used in the sample, and therefore serves as a negative control area. FIGS. 2 and 3 are illustrative of the resulting change in the label emission pattern in the medium 2 when the target analyte is present in the sample. FIG. 2 shows the result of a relatively low level of target analyte in the sample which will produce a plurality of more highly labeled colonies 4 surrounded by halos 6 of lower level label in the medium 2. FIG. 3 shows the result when there is a relatively high level of target analyte in the sample. It will be noted from FIGS. 2 and 3 that one can count the colonies 4, and since the volume of the sample inoculum and the size of the field of medium 2 can be known, one can derive a concentration of analyte per unit volume of the sample by following the procedure of this invention. FIG. 4 is a pictograph of the emission intensity from the label that will be detected by an auto-analyzing instrument as it performs a linear scan of the medium. The trace 8 represents the emission levels from the label in the medium; the dips 10 represent the low levels of label signal emission emanating from the "dim" halos 6; and the peak 12 represents the high level of label signal emission emanating from the "bright" colonies 4.

The following are examples of target analytes which can be detected utilizing the technique of this invention, and reagents for use in detecting each analyte.

EXAMPLE 1

In the case of the detection of *E.coli* 0157:H7 from a food or environmental source, a LASM is made by covalently binding a fluorophore, such as fluorescein or Texas Red, to an antibody which is specific to the 0157:H7 organism. The LASM is mixed with a growth medium such as Muller-Hinton agar, MacConkey's Sorbital medium, or the like, such that there results a sufficient concentration of the LASM to either appear visible when illuminated by light of an appropriate wavelength, or be readily measurable by an imaging system. In the case of visual detection, fluorescein is the preferred label. When a photometric analysis protocol is used, the label can be a sulphorhodamine label, or a Cy3, Cy5, or a Cy7 label, the latter of which Cy labels emit signals in the red, or near infrared, wavelengths, and are not detectable by the human eye, but which are photometrically detectable.

A plate is poured with a thickness of preferably 0.5 millimeter of the medium/LASM mixture for use in an instrumental detection format; or with about 1.0 millimeter thick layer of the mixture for use in a visual detection format. If the sample is from a clinical source, it may be plated directly on the medium. If the sample is from a food source, the food source will preferably be dispersed in a sterile solution and then filtered to remove visible particulate materials from the sample. Samples from environmental sources can be treated in the same manner as food samples.

After the sample is incubated at a temperature of about 35° C., the plated sample will be periodically examined as described above. Samples suspected of containing only a few organisms may be concentrated by, for example, filtering a volume of material to be tested and then placing the filter on the medium. Inasmuch as the filter is by definition permeable, the LASMs can pass through the filter and attach to the organisms growing thereon, as if the organisms were growing on the surface of the medium itself.

EXAMPLE 2

In the case of the detection of *Listeria monocytogenes*, such as from a sample of cheese, the analysis is preferably performed in accordance with Example 1 above, except that the LASM is made by covalently binding the fluorophore or other dye to an antibody specific to the Listeria organism. The LASM is mixed with a growth medium such as Esculin-based gram positive selective agar. After the sample being analyzed is inoculated onto the medium, the plate is incubated at 35° C. The plate is then periodically visually or photometrically examined as described above.

EXAMPLE 3

In the case of the detection of *Salmonella typhi*, such as from a sample of food, water, or a clinical source, the analysis is preferably performed in accordance with Example 1 above, except that the LASM is made by covalently binding the fluorophore or other dye to an antibody specific to the *Salmonella typhi* organism. The LASM is mixed with a growth medium such as Bismuth sulfite agar or Hektoen enteric agar. After the sample being analyzed is inoculated onto or into the medium, the plate is incubated at 35° C. The plate is then periodically visually or photometrically examined as described above.

EXAMPLE 4

In the case of the detection of the yeast *Candida albicans* from a clinical sample, the analysis is preferably performed in accordance with Example 1 above, except that the LASM is made by covalently binding the fluorophore or other dye to an antibody or lectin specific to the *Candida albicans* organism. The LASM is mixed with a growth medium such as a Sabouraud's dextrous agar medium. After the sample being analyzed is inoculated onto the medium, the plate is incubated at 35° C. The plate is then periodically visually or photometrically examined as described above.

It will be readily appreciated that the above-described method and paraphernalia can be utilized to detect the presence or absence of various microbes which may be present in a sample being analyzed. The creation of the localized dimly labeled halos which surround brightly labeled target microbe colonies that may form in the growth medium allows either visual or photometric detection, and counting of any formed target microbe colonies in the growth medium When utilized, the selective nature of the growth medium will enhance target microbe colony growth and suppress non-target microbe colony growth. The technique can be used to assess the concentration of target microbes in the sample by simply counting the formed colonies and recording the volume of sample which is inoculated onto or into the growth medium. Sequential readings can be taken from identical areas of the medium to detect changes in local LASM concentration, which changes are related to target analyte growth.

Since many changes and variations of the disclosed embodiments of the invention may be made without departing from the inventive concept, it is not intended to limit the invention otherwise than as required by the appended claims.

We claim:

1. An assembly for use in visually or photometrically detecting one or more live target microbial organism analyte(s) in a sample of a material which is suspected to contain the target analyte(s), said assembly comprising:
    a) a sample container;
    b) a growth-supporting medium in said sample container, said medium being operative to support metabolic replication of said target analyte(s) so as to enable said target analyte(s) to form target analyte colonies in or on said medium, and said medium being a medium which restricts intra-medium migration of target analyte colonies which form in or on said medium; and
    c) one or more labeled target analyte-specific material(s) (LASM(s)) which are homogeneously dispersed throughout said growth-supporting medium and which LASM(s) migrate within said growth-supporting medium toward target analyte colonies which form in or on said growth-supporting medium so as to differentially highlight said target analyte colonies.

2. The assembly of claim 1 wherein said growth-supporting medium is a medium which promotes metabolic target analyte colony formation and which inhibits non-target analyte metabolic colony formation in or on said growth-supporting medium.

3. The assembly of claim 1 wherein said target analyte(s) include *E.coli* 0157:H7; said LASM(s) include an *E.coli* 01 57:H7-specific antibody coupled with a detectable label; and said growth-supporting medium is a growth-supporting medium selected from the group consisting of a Muller-Hinton agar Kirby-Bauer medium; and a MacConkey's Sorbital medium.

4. The assembly of claim 3 wherein said label is a label selected from the group consisting of fluorophores, Cy-3, Cy-5, and Cy-7.

5. The assembly of claim 4 wherein said label is a sulforhodamine.

6. The assembly of claim 4 wherein said label is a fluorescein.

7. The assembly of claim 1 wherein said target analyte(s) include *Listeria monocytogenes*; said LASM(s) include a *Listeria monocytogenes*-specific antibody coupled with a detectable label; and said growth-supporting medium is Esculin-based gram positive selective agar.

8. The assembly of claim 7 wherein said label is a fluorophore.

9. The assembly of claim 8 wherein said fluorophore is a sulforhodamine.

10. The assembly of claim 8 wherein said fluorophore is a fluorescein.

11. The assembly of claim 1 wherein said target analyte(s) include *Salmonella typhosa*; said LASM(s) include a *Salmonella typhi*-specific antibody coupled with a detectable label; and said growth-supporting medium is an agar medium selected from the group consisting of Bismuth sulfite agar and Hektoen enteric agar.

12. The assembly of claim 11 wherein said label is a fluorophore.

13. The assembly of claim 11 wherein said fluorophore a sulforhodamine.

14. The assembly of claim 11 wherein said fluorophore is a fluorescein.

15. The assembly of claim 1 wherein said target analyte(s) include *Candida albicans*, said LASM(s) include a *Candida*

*albicans*-specific antibody or lectin which is combined with a detectable label; and said growth-supporting medium is a Muller-Hinton agar Kirby-Bauer medium.

16. The assembly of claim 15 wherein said label is a fluorophore.

17. The assembly of claim 16 wherein said fluorophore is a sulforhodamine.

18. The assembly of claim 16 wherein said fluorophore is a fluorescein.

19. An assembly for use in photometrically detecting one or more live target microbial organism analyte(s) in a sample of a material which is suspected to contain the target analyte(s), said assembly comprising:

a) a sample container;

b) a growth-supporting medium in said sample container, said growth-supporting medium being operative to support metabolic replication of said target analyte(s) so as to enable said target analyte(s) to form target analyte colonies in or on said medium, and said medium being a medium which restricts intra-medium migration of target microbial analyte colonies which form in or on said medium; and c) one or more labeled analyte-specific material(s) (LASM(s)) which are homogeneously dispersed throughout said growth-supporting medium and which LASM(s) migrate within said growth-supporting medium toward target analyte colonies which form in or on said growth-supporting medium so as to differentially highlight said target analyte colonies.

20. The assembly of claim 19 wherein said growth-supporting medium is a medium which promotes metabolic target analyte colony formation and which inhibits metabolic non-target analyte microbial colony formation in or on said growth-supporting medium.

21. The assembly of claim 19 wherein said LASM(s) include a photometrically detectable label selected from the group consisting of Cy-3, Cy-5, and Cy-7.

22. A method for photometrically detecting one or more live target microbial analyte(s) in a sample of a material which is suspected to contain the target analyte(s), said method comprising:

a) the step of providing a sample container;

b) the step of providing a growth-supporting medium in said sample container, said growth-supporting medium being a medium which is operative to support metabolic replication of said target analyte(s) so as to enable said target analyte(s) to form target analyte colonies in or on said medium, and said being a medium which restricts intra-medium migration of target microbial analyte colonies which form in or on said medium;

c) the step of providing one or more labeled analyte-specific material(s) (LASM(s)) which are homogeneously dispersed throughout said growth-supporting medium, said LASM(s) being photometrically detectable and which LASM(s) migrate within said growth-supporting medium toward target analyte colonies which form in or on said growth-supporting medium;

d) the step of inoculating the material(s) being analyzed onto or into said growth-supporting medium; and e) the step of photometrically scanning the inoculated medium for the presence or absence of brightly labeled target analyte colonies.

23. The method of claim 22 wherein said growth-supporting medium is a medium which promotes metabolic target analyte colony formation and which inhibits metabolic non-target analyte colony formation in or on said growth-supporting medium.

24. The method of claim 22 wherein said LASM(s) include a photometrically detectable label selected from the group consisting of Cy-3, Cy-5, and Cy-7.

25. The method of claim 22 wherein said brightly labeled target analyte colonies are surrounded by dimly labeled halos in said medium.

26. The method of claim 22 wherein sequential readings are taken from identical areas of the medium to detect changes in local LASM concentration which changes are related to metabolic target analyte growth.

\* \* \* \* \*